(12) United States Patent
Lemke et al.

(10) Patent No.: US 6,471,172 B1
(45) Date of Patent: Oct. 29, 2002

(54) FIXING DEVICE FOR AT LEAST ONE OPERATING ELEMENT SUITABLE FOR APPLICATION IN STERILE AREAS IN SURGICAL OPERATIONS, SUCH AS A SURGICAL INSTRUMENT

(76) Inventors: Norbert Lemke, Danziger Strasse 21, D-82194 Gröbenzell (DE); Rosemarie Lemke, Danziger Strasse 21, D-82194 Gröbenzell (DE)

( * ) Notice: Subject to any disclaimer, the term of this patent is extended or adjusted under 35 U.S.C. 154(b) by 56 days.

(21) Appl. No.: 09/691,120

(22) Filed: Oct. 19, 2000

(30) Foreign Application Priority Data

Oct. 19, 1999 (DE) ......................................... 199 50 440

(51) Int. Cl.⁷ ................................................ E04G 3/00
(52) U.S. Cl. ................................ 248/278.1; 248/125.7; 600/228
(58) Field of Search .......................... 248/278.1, 125.7; 128/20, 849, 852, 855; 600/228, 102, 137; 24/66.1, 303

(56) References Cited

U.S. PATENT DOCUMENTS

| | | | |
|---|---|---|---|
| 4,854,301 A | | 8/1989 | Nakajima |
| 5,184,601 A | * | 2/1993 | Putman .................... 312/209 |
| 5,224,680 A | | 7/1993 | Greenstein et al. |
| 5,351,676 A | * | 10/1994 | Putman .................... 200/5 R |
| 5,421,722 A | * | 6/1995 | Stemmann .................. 335/302 |
| 5,425,763 A | * | 6/1995 | Stemmann .................. 335/285 |
| 5,428,331 A | * | 6/1995 | Graner et al. ............... 118/500 |
| 5,571,072 A | * | 11/1996 | Kronner .................. 248/279.1 |
| 5,732,712 A | | 3/1998 | Adair |
| 5,907,664 A | * | 5/1999 | Wang et al. ................ 600/101 |
| 5,957,423 A | * | 9/1999 | Kronner .................. 248/278.1 |
| 5,970,980 A | * | 10/1999 | Adair ........................ 128/849 |

* cited by examiner

*Primary Examiner*—Leslie A. Braun
*Assistant Examiner*—Ingrid Weinhold (57) ABSTRACT

A fixing device is disclosed for at least one operating element or fixing element suitable for application in sterile areas in surgical operations, which is largely freely positioned in three dimensions and supported for fixing, while the sterile area is separated from the non-sterile area substantially by a sheet-like covering. A holding device is provided which is located in the non-sterile area and which, while being at least separated by the covering, enters into an operative connection via an active surface with the operating or fixing element, with the operative connection being based on magnetic forces.

21 Claims, 4 Drawing Sheets

FIXING DEVICE FOR AT LEAST ONE OPERATING ELEMENT SUITABLE FOR APPLICATION IN STERILE AREAS IN SURGICAL OPERATIONS, SUCH AS A SURGICAL INSTRUMENT

BACKGROUND OF THE INVENTION

1. Field of the Invention

The invention relates to a fixing device for at least one operating element or fixing element suitable for application in sterile areas in surgical operations, which is largely freely positioned in three dimensions and supported for fixing, while the sterile area is separated from A non-sterile area substantially by a sheet-like covering means, 2. Description of the Prior Art The performance of endoscopic operations, preferably on the human body, requires the physicians involved in the surgical operation to handle the endoscopic surgical cases precisely which are introduced into intracorporeal cavities through openings in the body. Particularly when surgical measures are taken through the abdominal wall several endoscopic instruments are required which must be operated independently of each other and which are to be handled each by different physicians involved in the operation. A viewing endoscope, which is normally connected to a video camera, is introduced into the body cavity for optically monitoring the operation; depending on the area of the operation this viewing endoscope is aligned with this area and appropriately positioned. Such optical monitoring of the surgical operations to be performed inside the body requires, however, a permanent tracking of the distal end of the video recording system having an endoscopic configuration, so that these instruments must be controlled and guided throughout the entire surgical operation. The surgical operations, which take a very long time, inevitably result in fatiguing of the physicians involved in the operation, particularly those who are merely dealing with the positioning and tracking of the respective instruments, specifically as these operations are monotonous activities which equally require, however, a maximum degree of concentration.

For relief of the operating staff from this strain, stand- or support-like arrangements have become known which permit the positioning of endoscopic instruments relative to a surgery area. These include support-like systems standing on the floor or provided for fastening on the operation table, which are equipped with a plurality of support arms whereof each is connected to joints, with the individual support joints being fixed by means of regulating screws or fixing mechanisms provided for rotational operation. Apart from the support systems suitable for manual operation, other support systems have become known, too, which are driven by an electric motor and which are positioned in three dimensions via an appropriate controller. All these known support systems are based on the common functional objective to position a surgical instrument, which is required for performing or monitoring an operation, near the intracorporeal operating area where the physician performs the surgical operation. To this end, the respective surgical operation is mounted on the distal terminal region of the support system, which must, on the one hand, be positioned with a minimum of obstacles in three dimensions, if possible, and, on the other hand, must be locked in a predetermined three-dimensional position whilst the locking must be easy to unlock again.

Apart from the different known support arrangements, which, are distinguished from each other by different structural mechanisms for fastening or locking, respectively, all known support arrangements are complex and expensive structures. Specifically, the purchasing costs play an important role in the selection of a handling system.

Another very important aspect in the structural design of the aforedescribed support or fixing devices is the possibility of sterilizing them, since they are envisaged for the application in the sterile section of operation rooms. Clamping or jointed connectors are tedious or complicated to sterilize due to their multi-part structure as a result of a great number of gaps and interstices. The support or fixing components are frequently surrounded by so-called sterile disposable sheathings which, however, render the operability of the individual support components substantially more difficult. Moreover, the necessity to use the sterile sheathings accounts for an additional cost factor, which is not small, particularly as at least one sheath is consumed for each operation.

SUMMARY OF THE INVENTION

The present invention improves a fixing device for at least one operating or fixing element suitable for application in a sterile area during operations, which is largely freely positioned in three dimensions and supported for fixing, in such a way that the expenditure for the fixing device to be used in the sterile area, which is incurred by sterilization in terms of operating technique and investment, is reduced to a minimum. Very expensive disposable materials such as those required in the known support or fixing devices should be entirely avoided. Apart therefrom, the fixing device permits an easy operability for the operating surgeon, in particular the complexity, which is required for the structure so that the fixing device with its support-like structure will be free three-dimensional positioning, and is as small and simple as possible. One essential aspect of the invention furthermore relates to the provision of a solution at the lowest costs possible, which mainly do not entail any operating and maintenance costs, or only slight costs, in everyday application.

The present invention takes the surgical operating towel or drape into consideration, which is used in all surgical operations and which separates the non-sterile area from the sterile area.

The surgical towels or drapes, which are mostly made of tissue (the explanation set forth hereinbelow applies on principle also to towels made of other materials or combinations of materials such as coated paper, synthetic towels, etc.), are mostly made of cotton or textile material dyed in green, and as such they are suitable for sterilization by appropriate washing processes and for repeated use. In surgical operations, sheet-like coverings of this kind are placed on the patient to be treated while an appropriate cut-out is left only on the body area where the surgical operation is to be performed. All the instruments and objects present above the sheet-like covering means are turned towards the operating surgeon and must be sterile whereas objects located underneath the sheet-like covering are required to satisfy only substantially lower demands in terms of sterility or no sterility requirements at all. The present invention makes use of this aspect.

In accordance with the present invention a fixing device for at least one operating element or fixing element suitable for application in the sterile area in surgical operations, which is largely free positioning in three dimensions and supported for being fixed, with the sterile area being separated from the non-sterile area substantially by means of a sheet-like covering, is improved by the provisions that a holding device is provided which is located in the non-sterile area and which comes into operative connection with the operating or fixing element via an effective area, while being at least separated by the covering, with the operative connection being based on magnetic forces.

The inventive fixing device is thus fundamentally composed of two component assemblies, i.e. those located in non-sterile condition underneath the covering and those located in the sterile area above the covering. The non-sterile components of the fixing means preferably comprise a fastening base which is configured either as a floor-mounted post or as clamping device for the releasable fixation on a fastening rail peripherally surrounding the operating table.

The holding device, which is preferably infinitely variably vertically adjustable about a vertical axis, is connected to the post or the clamping device, co-operating with the latter for forming a single unit. The holding device is configured as a permanent magnet in a simplest design, which comprises a plane, pan-shaped or concave-spherical effective area. Moreover, the option is provided that it is possible, in addition to the infinitely variable vertical adjustability of the holding device, to incline the holding device relative to a horizontally extending plane in such a way that the effective area of the holding device takes a position inclined relative to the horizontal, preferably at an inclination by 45°.

As an alternative to the use of a permanent magnet as a holding device, a solenoid is equally suitable which has magnetic forces determined as a function of the current supplied to the solenoid; as a result, the solenoid can be switched at least between an ON and an OFF state and moreover the solenoid can be continuously controlled between the ON and OFF states, which means that the magnetic field strength can be controlled to a maximum field strength level in an infinitely variable manner.

The non-sterile components of the fixing device are preferably disposed in the immediate vicinity of the operating table so that the operation drape for sterile covering of the patient lying on the operating table for treatment covers, at the same time, also the holding device with the corresponding fastening provisions. The operating drape, which presents a cut-out merely at the site of the surgical operation, has normally an integral design without any further discontinuities. Hence the operating drape ensures a largely reliable and large-area separation of the sterile area from the non-sterile area, a characteristic which the fixing device of the invention uses. On principle operating or fixing elements of any design, which present ferromagnetic properties in their turn, may be fastened on the operation towel resting on the effective area of the holding device, which elements may be fixed on the holding device in dependence on the intensity of the magnetic forces. It is thus fundamentally possible to place a supporting rod made of a ferromagnetic material on an effective area of the holding device having a planar configuration, merely separated by the covering, for three-dimensional fixing of the device. On the end of the supporting rod, which faces the operating area, connecting mechanisms known per se and having a joint-like configuration may be provided for fastening further operating elements having a support-like design, with the possibility of mounting an optical viewing endoscope on the distal terminal region of these further elements for monitoring a surgical operation. Like all other tools for application in the sterile section, the operating or fixing elements, respectively applied in the sterile areas, i.e. above the covering, are governed by the requirement of sterilizability which should be as easy and rapid as possible. This requirement, however, can be satisfied only in an unsatisfactory manner, if at all, with joint mechanisms of the known type which comprise two operating elements having a rod-shaped design for coupling to each other in such a way that they can be occupied relative to each other about all three-dimensional axes, largely without any impairment or interference, specifically as the structure of these known mechanisms is too complex and provided with a great number of gaps wherein the interstices cannot be completely sterilized.

To satisfy the requirement of a complete sterilization particularly suitable operating elements as joint connectors are provided with a pan-shaped joint structure of a concave design on one of their ends, which is made of a ferromagnetic material or comprises at least a ferromagnetic material. For reasons of complete sterilizability, the ferromagnetic material must have an annealing (Curie) temperature higher than 250° C.

For coupling a second operating element, preferably of a rod-shaped design, this element presents a spherical counter-contour on one end thereof which is precisely fitted into the spherically designed pan contour of the first operating element. Depending on the selected material and the size of the joint form, the magnitude of the magnetic forces can be selectively set between the operating elements held together by magnetic forces, which ensure, on the one hand, a permanent jointing of both operating elements and permit, on the other hand, a rotational mobility through almost 360° relative to each other, which the operating surgeon desires.

The foregoing statements referred to the simplest embodiment of a fixing device of the inventive configuration, i.e. the mere covering of the magnetic active surface of the holding by the covering configured as operation drape and an operating element disposed directly thereon, which is preferably configured in the manner of a supporting rod.

On account of the immediate contact with the covering, the operating element, which enters into a magnetic operative connection with the holding, is able to cause such a strong mechanical strain on the covering, which is preferably made of a textile tissue, due to relative movements occurring as a result of the operating surgeon's manipulations for three-dimensional positioning of the endo-surgical instrument mounted on the distal end of the support system, such that wear of the covering cannot be precluded.

Moreover, with the aforementioned relative movements between the operating element and the active surface of the holding device, creases may be formed in the means which may lead to maladjustment or at least to an impeded free mobility of the support system. For avoidance of such creases, it is expedient to place an additional cap element on the holding device covered by the covering, which cap element covers at least the active surface of the holding device and is placed or plugged onto the holding device with the covering located immediately there above.

The cap element as such is provided with a cap cover which is preferably made of a ferromagnetic material and comprises a base plate into which a groove is machined which has an inside contour conformed to the outside contour of the operating element. In this manner it is possible, for instance, to insert a rod-shaped operating element into the groove in the ferromagnetic base plate of the cap element, for reasons of an improved fixing, where it is magnetically fixed. As a function of the magnetic forces which may be continuously controlled, for instance, when a solenoid is used, the operating element may be displaced along the longitudinal axis of the groove and rotated about the holding device, which presents preferably a circular outside periphery, together with the complete cap element. A non-magnetic cover plate is provided for an upper closure of the groove, which is designed to be open on one side within the base plate, which non-magnetic plate is placed on the base plate but does not enter itself into a magnetic interaction with the magnetic field caused by the holding device, so that the lines of the magnetic field will predominantly enter into the base plate and the operating element inserted into the base plate in a non-weakened form. It is ensured in this way that the major fraction of the magnetic flux serves to fix the operating element inserted into the base plate and is not oriented by fixing device components not participating in the fixing action, which would weaken the magnetic field.

To ensure a controlled rotational mobility of the cap element on the holding device covered by the covering without any risk of crease formation in the covering between the holding device and the cap element, pin-like projections are disposed in the area of the peripheral edge on the cap element, preferably at equal distances from each other, so that the pin-like projections will radically surround the holding device along a peripheral edge thereof when the cap element is placed onto the holding device. Due to the spaced arrangement of the pin-like projections on the cap element, the creases which may be formed during the placement of the cap element onto the sheet-like covering may largely freely unfold in the interstices between the pin-like projections. As a result, the sheet-like covering is actually stretched without any creases over the entire active surface of the holding device, which is covered by the cap element, and remains also free of creases even when the cap element is turned about the holding. The pin-like projections present a substantially round design in the manner of a finger so that the creases of the sheet-like covering means cannot be clamped between the projections and the holding but may rather be formed with a free fall between the pin-like projections. As the cap element with its base plate rests over a large area on the entire active surface of the holding element, while being separated by the sheet-like covering, the covering is subjected to a slight mechanical strain only even when the cap element is rotated about the holding so that wear of the covering can be largely precluded. Moreover, the sheet-like covering serves at the same time as an intermediate sliding layer between the base plate of the cap element and the active surface of the holding device so that, depending on the prevailing magnetic forces, the operating surgeon can rotate the cap element without any clamping. This free mobility is indispensable particularly for fine positioning of a video recording unit mounted on the distal end section of the operating elements having a support-like structure.

The fixing device of the invention serves not only for the aforedescribed releasable fixed connection of an operating element having a support-like structure on a holding disposed invariably relative to or on the operating table but can also be used for fastening or fixing the operating drape, for instance on the operating table or in the immediate vicinity thereof.

A holding device which has, for instance, a pan-shaped magnetic active surface may also serve as fixing element for the operating drape, which rests on the holding device and is fixed by means of a fixing element, which may be configured, for instance, as a sphere engaging with precise fit into the pan-shaped active surface of the holding device. The holding device is located in the non-sterile section and the fixing element, which has a spherical design, may be placed on the covering for engagement in the holding device from the sides of the sterile area. Fixing elements having such a configuration are furthermore easy to sterilize and suitable for manifold applications for fixing tasks in surgical operations.

BRIEF DESCRIPTION OF THE INVENTION

The invention will be described hereinbelow by exemplary embodiments, without any restriction of the general inventive idea, with reference to the drawing wherein:

FIGS. 1a, b are schematic side and plan view of a holding means,

FIG. 1c is a schematic cross-section taken through a cap element,

DESCRIPTION OF THE PREFERRED EMBODIMENT OF THE INVENTION

FIG. 1a illustrates a side view of a holding device provided with a body section of a cylindrical design into which a magnet 2 of an annular design is integrated. It is fundamentally possible to configure the magnet 2 either as permanent magnet or as a solenoid; what is essential is the aspect that the magnetic field 3 of the magnet 2 can freely propagate over the active surface 4 of the holding device. Opposite the active surface 4, a conical section is provided on the holding device 1 which may be fixedly connected to a support structure not illustrated here, which may be fixed for invariable positioning of the holding device 1 on the floor or on a mounting bar of an operation table by means of an appropriate system.

The active surface 4 of the holding device 1 is illustrated as area having a planar configuration in the plan view in FIG. 1b. The magnet or solenoid 2, which has an annular cross-section, generates a magnetic field, which is substantially oriented in an upward direction on the active surface 4. Moreover, the holding device 1 presents a circular outside periphery 5 which contributes expediently to the easy operability of the overall fixing device, as will be described in more detail in the following.

FIG. 1c illustrates the cap element 6 in a cross-sectional view, in illustrative contrast with FIG. 1a. The cap element 6 consists substantially of a base plate 7 which projects laterally beyond the active surface 4 of the holding device 1 and which has an underside 71 which is equally of a planar design, like the active surface 4. The base plate 7 moreover comprises, on its upper side 72, a groove 73 designed to be open on one side and having an inside contour which is largely conformed to the outside contour of the rod-shaped configuration of an operating element 8. The mutual contour matching, which corresponds to a hexagonal shape in the case of the embodiment according to FIG. 1c, serves to ensure a largely intimate and large-area of physical contact between the operating element 8 and the base plate 7, which leads to an improved magnetic fixation. A rectangular or square cross-sectional shape of the groove with a corresponding respective cross-sectional shape of the operating element 8 to be inserted into the groove 73 is equally suitable.

The base plate 7 is homogenously made of a ferromagnetic material so that the magnetic field 3 can be largely completely penetrated into the base plate 7 when the base plate 7 is appropriately approached towards the active surface 4 of the holding device 1. For an optimization of the operating element 8 inside the groove 73 by means of magnetic forces, the depth of the groove 73 is very wide, compared against the thickness of the base plate 7, so that only the slightest distance possible exists between the operating element 8, which is inserted into the groove, and the active surface 4 of the holding element. In this manner, the magnetic field penetrates into the operating element 8 made of a ferromagnetic material largely without any weakening so as to fix the operating element, together with the base plate 7, against the active surface 4 of the holding device 1. It is, however, also possible to design the groove 73 in a way that to open towards the underside 71.

To prevent the operating element 8 from potential vertical tilting inside the groove 73 a cover plate 9 is releasably fixed on the base plate 7, which, in turn, is made of a non-ferromagnetic material and does hence not contribute to any weakening of the magnetic field.

Figure 1:
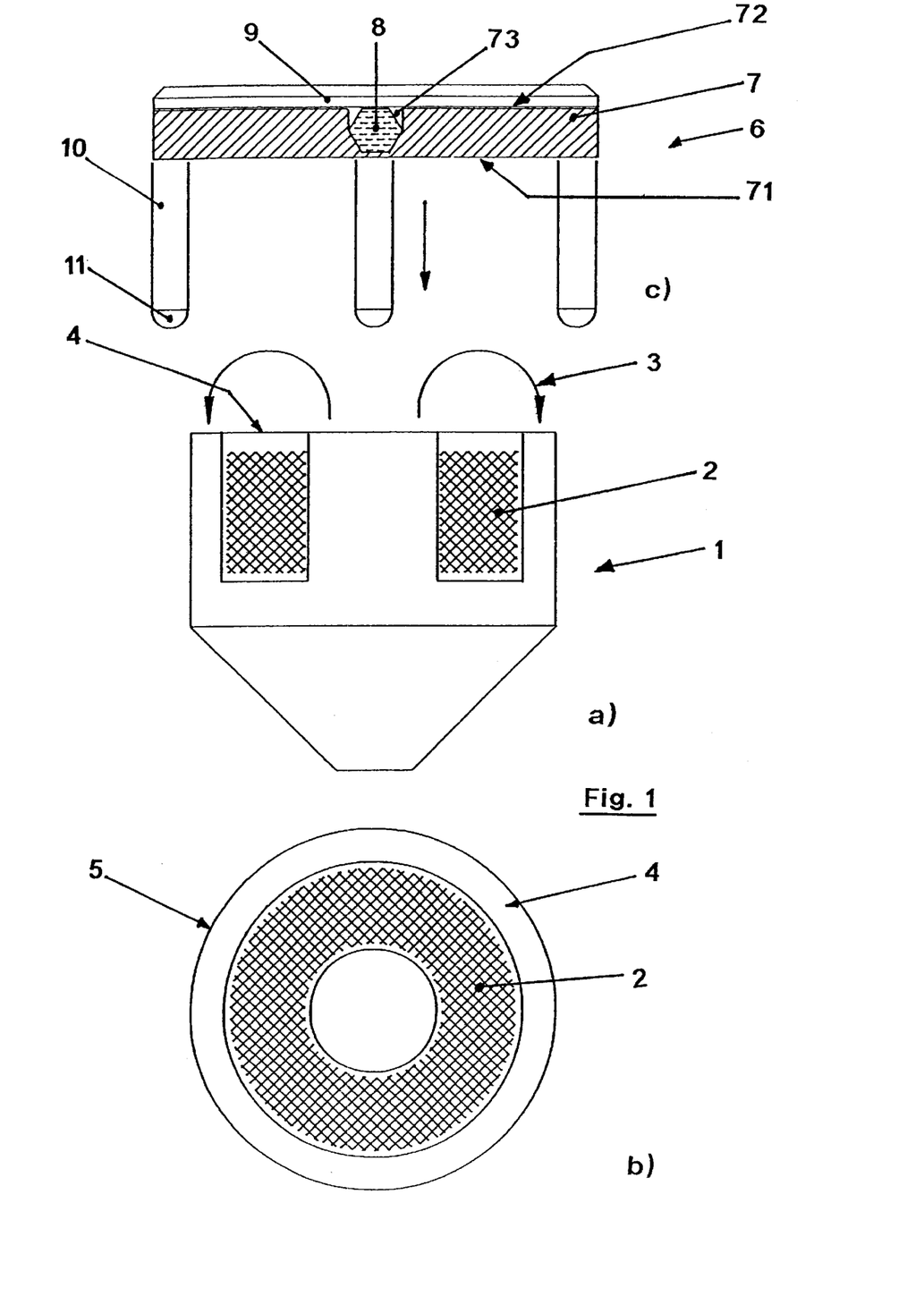

Furthermore, the cap element 6 presents pin-like projections 10 which project vertically from the base plate 7 downwards in the region of the peripheral edge of the element, which is equally circular; these projections are configured in the manner of round fingers having rounded caps 11 and, after placement of the cap element 6 onto the holding device 1 (cf. direction of the arrow), surround this element almost without any clearance along its peripheral edge. The cap element 6, which is seated on the holding device 1, may be rotated about the holding device 1, with the number and arrangement of the pin-like projections 10 having to be selected in such a way that a safe rotation of the cap element 6 relative to the fixed holding device 1 is possible without the risk of a possible clamping or tilting, respectively. A sheet-like covering is provided, which is not illustrated in FIG. 1 and which is inserted between the cap element 6 and the active surface 4 of the holding device 1. In this respect reference is made to the discussion of FIG. 3.

Figure 2:
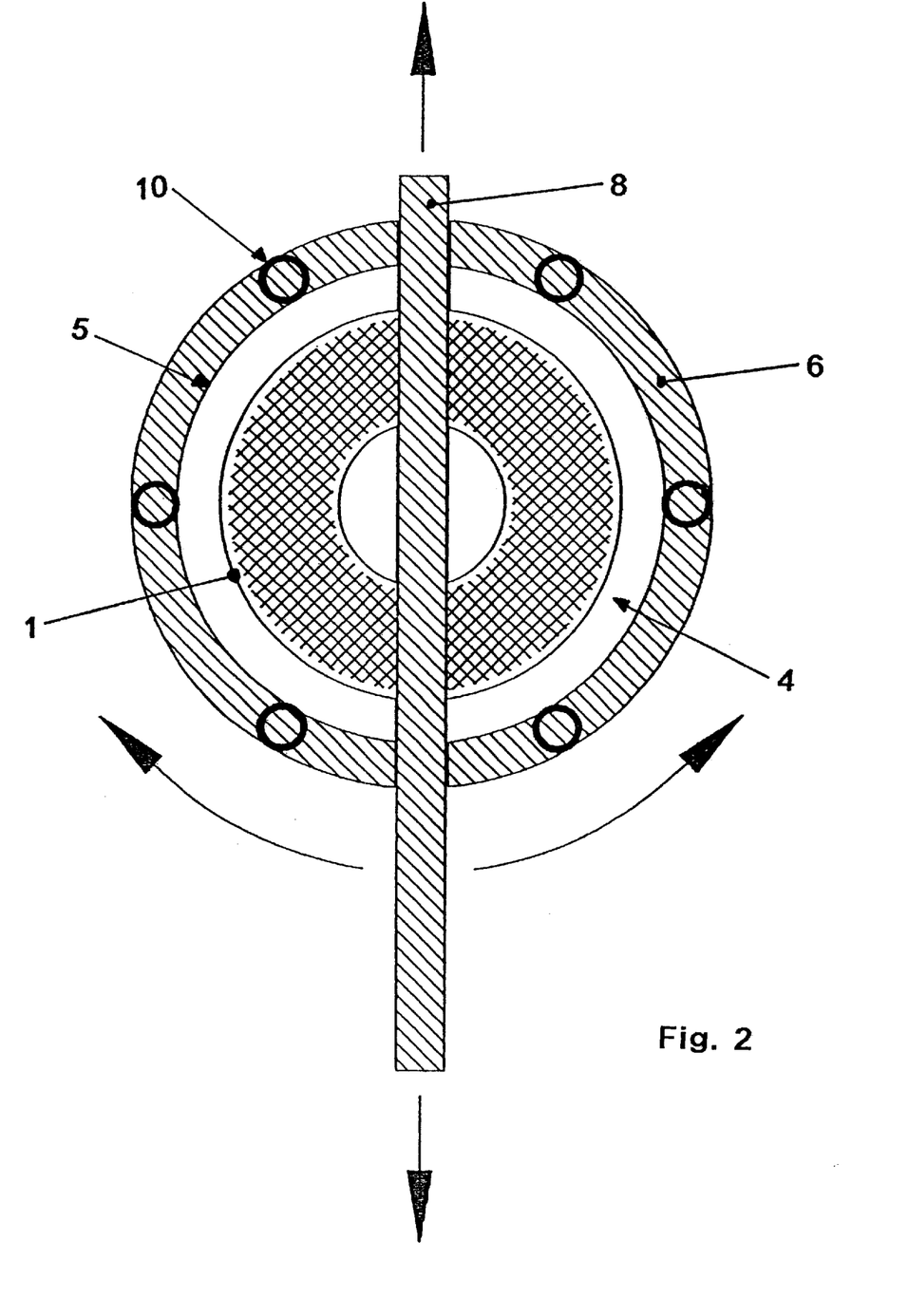
FIG. 2 illustrates a schematic cross-section through an operating element inserted into a cap element.

FIG. 2, which illustrates a cross-sectional view of the cap element 6 into which the operating element 8 is introduced and which rests, together with the cap element 6, on the active surface 4 of the holding device, shows a preferred arrangement of the pin-like projections 10 on the cap element 6. Six projections 10 are equidistantly provided in the region of the peripheral edge of the cap element 6 and enclose therein the peripheral edge 5 of the holding device, largely with a precise fit. The geometric arrangement of the projections 10 on the cap element 6 should, however, take an insertion of a sheet-like covering between both elements into account so that a free rotation of the cap element 6 relative to the holding means 1 will also be possible with a cloth disposed between the two components.

Due to the magnetic forces generated by the magnet 2, both the cap element 6 and the rod-shaped operating element 8, which is inserted into the cap element 6, are fixed relative to the holding device 1. In the preferred case of application of a solenoid the strength of the magnetic field is variable so that, on the one hand, the operating element 8 can be guided along its longitudinal extension for-movement relative to the cap element 6 and, on the other hand, the cap element 6 may freely rotate through 360° about the holding means 1 by means of the operating element 8 (cf. in this context the respective arrows in FIG. 2 which indicate the degrees of freedom in the movements of the individual components). When a desired position has been achieved, the operating surgeon may increase the strength of the magnetic field of the solenoid so that the individual components of the fixing device are fixed in an almost immobilized manner. The solenoid is controlled by means of the common automatic control circuits which, in their turn, are provided in the non-sterile section in an operating theatre.

Figure 3:
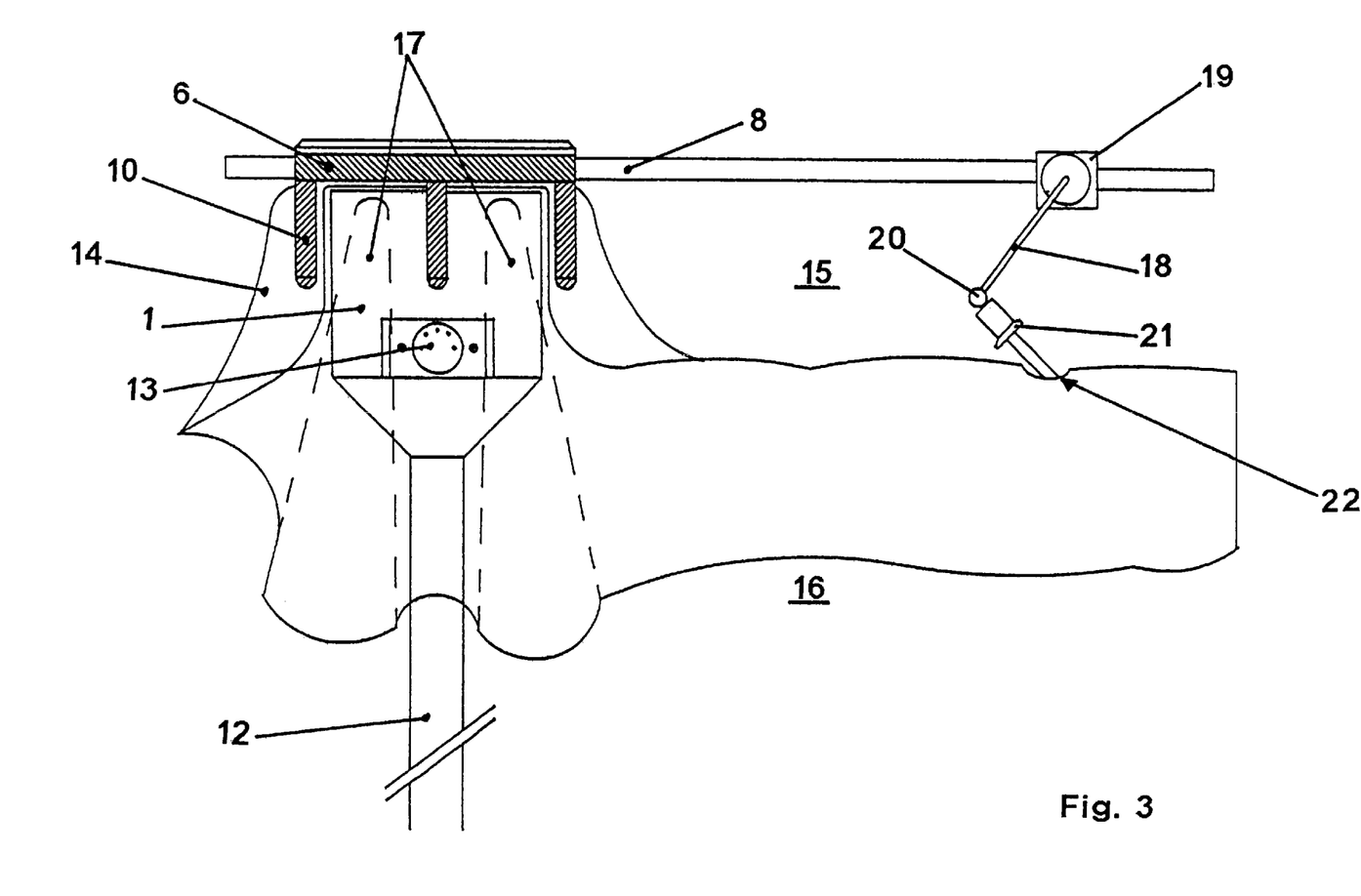
FIG. 3 shows the fixing device in application during a surgical operation, with sheet-like covering means, as well as FIG. 4 illustrates the potential movements of the fixing device in operative application.

FIG. 3 is a schematic side view of the complete arrangement of an expedient configuration of the fixing device of the invention with the holding device 1 fixedly connected in three dimensions on a support 12. The support or post 12 is provided with a lifting device suitable for vertical adjustment (which is not illustrated here) so that the fixing device of the invention may be moved into any vertical position. In an embodiment illustrated in FIG. 3, the holding device 1 comprises an electronic connector 13 on the cylindrically shaped body section, which may be used, for instance, to establish the controlled power supply for a solenoid integrated into the holding device 1. The operation drape or towel or a sheet-like covering 14 is applied directly on the holding device 1, which separate the sterile area 15 from the non-sterile area 16 provided underneath the covering 14. The cap element 6, which is over the operation drape 14, is seated on the holding device 1 directly. The fabric creases 17 forming in the operation drape 14 in the interstices between the web-like projections 10 drop freely downward. The possibility of fabric crease formation between the web-like projections 10 ensures a crease-free formation of the operation drape 14 directly between the active surface 4 of the holding device 1 and the base plate 7 of the cap element 6. Even a rotation of the cap element 6 about the stationary holding device 1 does not result in a large-area slipping of the operation drape 14 but the operation drape 14 rather remains without movement between both components.

A rod-shaped operating element 8, consisting of a ferromagnetic material projects, into the cap element 6; this operating element 8 serves as a supporting rod for another operating element 18 designed in the manner of a support. The support-like operating element 18 is connected to the operating element 8 by means of a joint unit 19 largely for rotational movement. An endo-surgical instrument 21 is mounted on the distal end of the support-like operating element 18 via a further joint unit 20, which instrument is passed and targeted through the operation drape 14 into an opening 22 in the body where it is precisely positioned in three dimensions. The operating surgeon, who is responsible for a precise three-dimensional positioning of the endo-surgical instrument 21 inside the body opening 22, deactivates the solenoid appropriately prior to a necessary variation of the position of the support system such that the fixing device permits the possible movements described in FIG. 2. The joint units 19 and 20 are provided with common self-fixing mechanisms. When the new position of the support system and particularly of the endo-surgical instrument 21 has been achieved, the fixing device 1 is newly fixed with an appropriate repeated activation of the solenoid.

In addition to the aforementioned vertical adjustment of the holding device 1, the holding device 1 may also be pivoted about a horizontally extending axis so that the active surface 4 of the holding device assumes an inclined position relative to the horizontal plane. Such a tilting mechanism may be implemented, for instance, by means of common snap-in.

Figure 4:
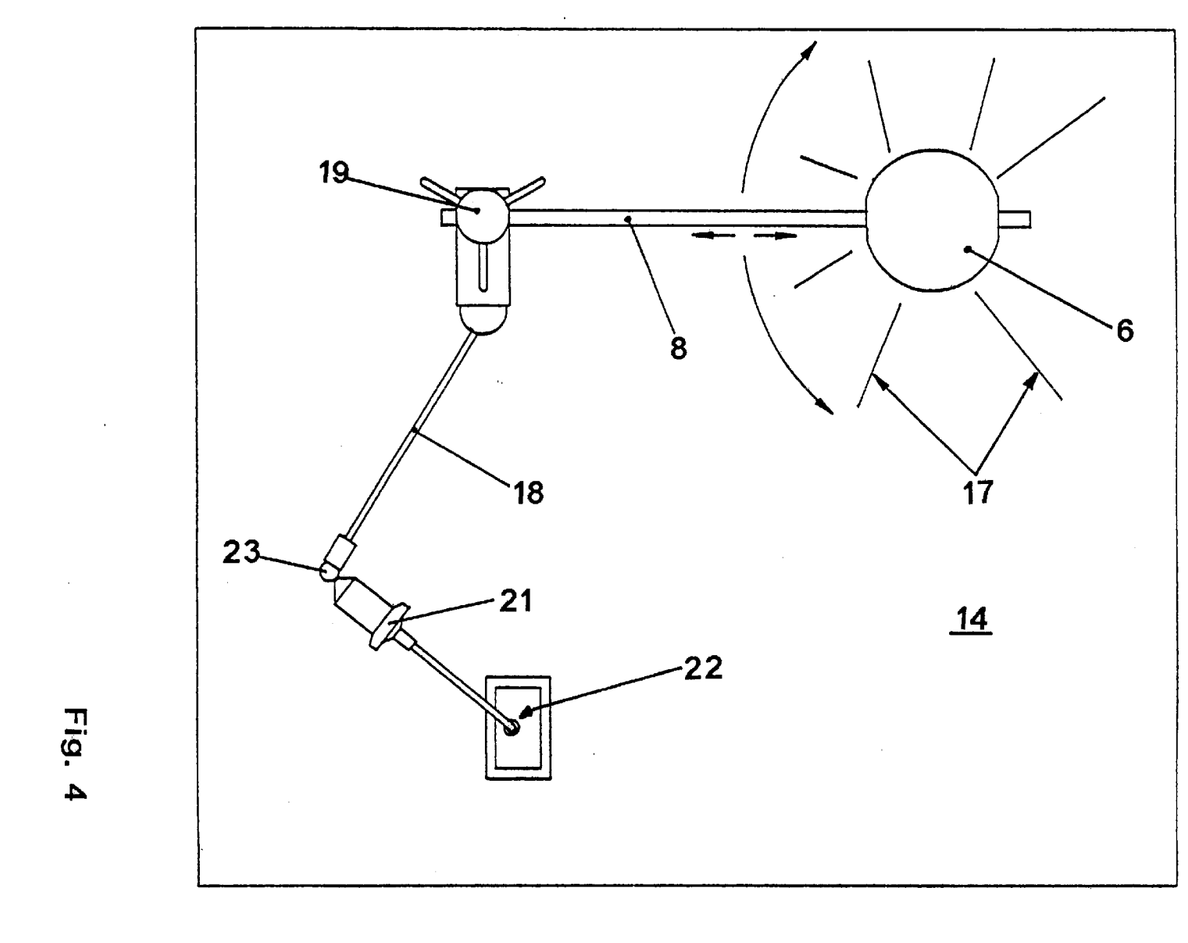

FIG. 4 shows a plan view of the arrangement shown in a side view in FIG. 3. The operating element 8 passes through the cap element 6 which is pushed over the operation drape 14, that is schematically shown in the illustration of FIG. 4 to cover the entire indicated rectangular area, and onto the holding means not visible here. The creases 17 in the cloth are schematically indicated. The components illustrated in FIG. 4 are thus completely located within the sterile area of an operating site. A clamping joint 19, known per se, is provided on the distal end of the rod-shaped operating element 8 and serves to mount a further operating element having a support-like structure. A pan-shaped contour, providing magnetic forces, is provided on the distal end of the support-like operating element 18, into which a sphere 23, which is provided on the proximal end of the endo-surgical instrument 21, is projecting. The sphere 23 as such is made of a ferromagnetic material and is fixed by the magnetic forces in the pan-shaped contour. The holding force for the endo-surgical instrument 21, which results from the magnetic force, must be so high that the instrument will be automatically retained in a preset cantilever position. The holding force must, however, not be so high that a manual operation will be impossible in a corresponding variation of the position.

The distal end of the endo-surgical instrument is passed through a cut-out in the operation drape 14 into a body opening 22 and appropriately positioned there.

The fixing device of the invention makes possible use of very easily sterilizable components in the sterile area for assistance in the performance of surgical operations. When the fixing device of the invention is employed, any further sterilization steps need not be performed, specifically as one essential aspect of the invention is the use of the operation drape, which is present in any surgical operation.

Frequently the case occurs that the operation drape must be fixed on the operating table. The inventive fixing device may serve to this end as well, which corresponds to a connecting element in the simplest configuration, which is provided on the distal end of the support-like operating element 18 according to FIG. 4. It is hence merely necessary to use a permanent magnet as holding, which is provided with a pan-shaped active surface and is disposed in the sterile area underneath the operation drape. By means of a sphere made of a ferromagnetic material, which is very easy to sterilize, the operation drape can be fixed at any site whatsoever.

LIST OF REFERENCE NUMERALS

| | |
|---|---|
| 1 | holding means |
| 2 | magnet/solenoid |
| 3 | magnetic field |
| 4 | active surface |
| 5 | round peripheral edge |
| 6 | cap element |
| 7 | base plate |
| 71 | underside |
| 72 | upper side |
| 73 | groove |
| 8 | operating element |
| 9 | cover plate |
| 10 | pin-like projection |
| 11 | rounded caps |
| 12 | support |
| 13 | electronic connector |
| 14 | sheet-like covering means, operation drape |
| 15 | sterile area |
| 16 | non-sterile area |
| 17 | crease in the cloth |
| 18 | support-like operating element |
| 19,20 | joint means |
| 21 | endo-surgical instrument |
| 22 | body opening |
| 23 | sphere |

What is claimed is:

1. A system used in performing in a sterile area a surgical operation which uses a covering to separate the sterile area from a non-sterile area comprising:

a body which is provided with a magnet which generates a magnetic field which emanates from a surface which faces the covering, the body being located in the non-sterile area when in use during the surgical operation;

a ferromagnetic element, which is located in the sterile area during the operation and is separated by the covering from the body during the operation, the ferromagnetic element including a surface which faces the covering during the operation, being rotatable relative to the body and being attracted to the body by the magnetic field being coupled to the element; and an elongated member which is retained in the ferromagnetic element during the surgical operation and is attracted by the magnetic field so as to resist moving of the elongated member longitudinally relative to the ferromagnetic element during the surgical operation; and wherein during the surgical operation, the elongated member is used for supporting at least one element used during the surgical operation.

2. A system in accordance with claim 1 wherein:

the body comprises an electromagnet which produces a variable magnetic field controlled to vary attraction of the ferromagnetic element and the elongated member during the surgical operation.

3. A system in accordance with claim 1 wherein:

the ferromagnetic element includes a channel with surfaces which engage corresponding surfaces of the elongated member, the member being fixed against rotation relative to the channel and being attracted to a position within the channel by the magnetic field but being movable longitudinally by application of a longitudinal force applied to the member.

4. A system in accordance with claim 1 comprising:

an endoscopic instrument supported by the elongated member during the surgical operation.

5. A system in accordance with claim 1 comprising:

a video camera supported by the elongated member during the surgical operation.

6. A system in accordance with claim 1 comprising:

the surfaces of the body and element are planar.

7. A system in accordance with claim 1 comprising:

the elongated member is rod-shaped, spherical, or disk-shaped.

8. A system in accordance with claim 1 comprising:

a support to which the body is attached which is vertically adjustable to vary a vertical position of the body during the operation.

9. A system in accordance with claim 1 comprising:

the body is positionable during a surgical operation so that the surface of the body is inclined from vertical and while the surface is in an inclined position, the body is fixable in the inclined position.

10. A system in accordance with claim 1 comprising:

the surface of the body is planar.

11. A system in accordance with claim 1 comprising:

the surface of the body has either a pan-shape or a concave-spherical shape.

12. A system in accordance with claim 1 comprising:

a cap which covers at least the surface of the body with the covering being in contact with the cap during the surgical operation.

13. A system in accordance with claim 12 wherein:

the cap is a non-magnetic material.

14. A system in accordance with claim 3 wherein:

the channel is open, has a depth measured from a top surface of the body which corresponds at least to a longest cross-sectional length of the elongated member.

15. A system in accordance with claim 1 comprising:

a plurality of projections which extend from spaced apart locations on an annular area of the ferromagnetic element and surround the body during the surgical operation.

16. A system in accordance with claim 15 wherein:

the projections are positioned on the annular area at a periphery of the body.

17. A system in accordance with claim 16 wherein:

the projections are equally spaced apart on the annular area.

18. A system in accordance with claim 17 wherein:

the projections are pins.

19. A system in accordance with claim 1 comprising:

a movable operating support, connected to the elongated element by a rotatable joint, with at least one element being connected to the movable operating support with a rotatable joint.

20. A system in accordance with claim 18 wherein:

the at least one element is an endoscopic instrument.

21. A system in accordance with claim 19 wherein:

the at least one element is a video camera.

* * * * *